(12) United States Patent
Dakka et al.

(10) Patent No.: US 8,691,713 B2
(45) Date of Patent: Apr. 8, 2014

(54) MOLECULAR SIEVE CATALYST TREATMENT

(75) Inventors: Jihad M. Dakka, Whitehouse Station, NJ (US); Hans K. T. Goris, Laakdal (BE); Stephen H. Brown, Bernardsville, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1285 days.

(21) Appl. No.: 11/912,758

(22) PCT Filed: May 26, 2006

(86) PCT No.: PCT/EP2006/005071
§ 371 (c)(1),
(2), (4) Date: Jun. 24, 2008

(87) PCT Pub. No.: WO2006/128649
PCT Pub. Date: Dec. 7, 2006

(65) Prior Publication Data
US 2009/0203862 A1    Aug. 13, 2009

(30) Foreign Application Priority Data

May 31, 2005  (GB) .................................. 0511051.5

(51) Int. Cl.
*B01J 38/04* (2006.01)
*C07C 2/12* (2006.01)

(52) U.S. Cl.
USPC ............. 502/34; 585/502; 585/520; 585/530; 585/532; 585/533

(58) Field of Classification Search
USPC ......... 502/34, 22; 505/53; 585/502, 520, 530, 585/532, 533, 446, 467
See application file for complete search history.

(56) References Cited

U.S. PATENT DOCUMENTS

| | | | |
|---|---|---|---|
| 3,823,085 A | | 7/1974 | Kochie |
| 4,062,801 A | | 12/1977 | Burton et al. |
| 4,417,086 A | | 11/1983 | Miller |
| 4,417,088 A | * | 11/1983 | Miller ........................... 585/533 |
| 4,533,648 A | | 8/1985 | Corrigan et al. |
| 4,550,090 A | | 10/1985 | Degnan et al. |
| 4,560,536 A | * | 12/1985 | Tabak ........................... 422/116 |
| 4,939,314 A | * | 7/1990 | Harandi et al. ................ 585/533 |
| 5,019,357 A | | 5/1991 | Harandi et al. |
| 5,059,738 A | | 10/1991 | Beech, Jr. et al. |
| 5,151,393 A | * | 9/1992 | Harandi et al. .................. 502/53 |
| 5,243,118 A | * | 9/1993 | Sanderson et al. ............. 585/515 |
| 5,998,687 A | * | 12/1999 | Woodle et al. ................. 585/449 |
| 6,143,942 A | | 11/2000 | Verrelst et al. |
| 6,525,234 B1 | * | 2/2003 | Dandekar et al. .............. 585/467 |
| 6,579,821 B1 | * | 6/2003 | Ginosar et al. .................. 502/31 |
| 2003/0073876 A1 | | 4/2003 | Subramaniam et al. |
| 2004/0063567 A1 | * | 4/2004 | Ginosar et al. .................. 502/34 |
| 2005/0014630 A1 | | 1/2005 | Dakka et al. |

FOREIGN PATENT DOCUMENTS

| | | |
|---|---|---|
| EP | 0 375 286 | 6/1990 |
| EP | 0 625 132 | 11/1994 |
| EP | 0 716 887 | 6/1996 |
| EP | 0 746 538 | 12/1996 |
| EP | 1 070 694 | 1/2001 |
| WO | WO 01/80995 | 11/2001 |
| WO | WO 03035584 A1 * | 5/2003 |
| WO | 2006/128650 | 12/2006 |
| WO | WO 2006/128649 | 12/2006 |

* cited by examiner

*Primary Examiner* — In Suk Bullock
*Assistant Examiner* — Bradley Etherton
(74) *Attorney, Agent, or Firm* — Leandro Arechederra, III

(57) ABSTRACT

Treatment at elevated temperature and advantageously superatmospheric pressure with an inert gas, especially nitrogen, rejuvenates molecular sieve catalysts deactivated by use in liquid-phase or supercritical or dense-phase olefin oligomerization, or by use in aromatic alkylation.

15 Claims, No Drawings

MOLECULAR SIEVE CATALYST TREATMENT

CROSS REFERENCE TO RELATED APPLICATIONS

This application is a national stage filing of International Patent Cooperation Treaty Application No. PCT/EP2006/005071 filed May 26, 2006, which claims priority from Great Britain Application 0511051.5 filed May 31, 2005, the disclosure of which is fully incorporated herein by reference.

FIELD OF THE INVENTION

This invention relates to catalysts used in liquid phase or supercritical or dense phase olefin oligomerization processes or in the alkylation of an aromatic compound with an olefinic alkylating agent, and especially to catalyst treatment. More especially, it is concerned with rejuvenation of used catalysts from such processes, in particular of crystalline molecular sieve catalysts.

BACKGROUND OF THE INVENTION

It is well known that the useful life of a catalyst is limited. In the case of a catalyst used in hydrocarbon conversion, for example, its active sites may be poisoned by contaminants in the feedstock or the sites may become blocked by the build-up of unwanted by-products of reaction. Further, a catalyst may be deactivated by incorrect storage conditions.

As examples of contaminants in hydrocarbon feedstocks there may be mentioned oxygen-, nitrogen-, and sulphur-containing compounds. It has been found that certain upstream processes in the petrochemical industry form nitriles that are deleterious to catalyst activity. It has recently been discovered that certain sulphur-containing compounds are deleterious, especially those with high desorption temperatures.

In molecular sieve-catalysed olefin oligomerization or aromatic compound alkylation processes, it has been found that carbonaceous deposits, typically of a higher molecular weight and often referred to as "coke", block not only the active sites on the surface of the molecular sieve, but also the pores of the catalyst, preventing access of reactants to active internal sites as well.

A spent catalyst may be discarded, but disposal may be economically or environmentally unacceptable. A catalyst may be regenerated, by which term is meant the restoration of the activity of the catalyst to or very near to its original activity. Many regeneration methods, however, require high temperatures involving the removal of the catalyst from the reactor, often to a remote location, and lengthy reactor downtime and often substantial expense may be involved. An alternative is catalyst rejuvenation, by which term is meant increasing the activity of a deactivated (a term used to include partially deactivated) catalyst, but not necessarily to its original activity. Rejuvenation methods may be carried out more easily than regeneration, resulting in decreased reactor downtime, in some instances in situ.

U.S. Pat. No. 4,550,090 describes the regeneration of a deactivated dewaxing catalyst, in particular a ZSM-5 type catalyst, including the removal of nitrogenous contaminants, by treatment of the catalyst with a base, e.g., $NH_4OH$, and solvent-extraction.

WO 01/80995 describes rejuvenating a crystalline molecular sieve, especially a SAPO or $AlPO_4$ type catalyst, deactivated by moisture by treatment with an anhydrous liquid or vapour.

U.S. Pat. No. 5,059,738 describes the reactivation of a catalyst in a process converting methanol to gasoline between about 300° C. and 400° C. in contact with a stream of inert purge gas. The inert gas may include nitrogen, light paraffinic hydrocarbons, and Group VIII gases of the Periodic Table of the Elements. The methanol to hydrocarbon conversion processes, such as the methanol-to-olefins (MTO) process and the methanol-to-gasoline (MTG) process, are known to occur via alkylation and dealkylation reaction steps involving aromatic intermediates. The "coke" formed in these processes therefore contain significant amounts of single up to 4 or 5 multiring aromatics. When the process uses a large pore open structure molecular sieve as catalyst, such as ZSM-5, single ring aromatics are sufficiently small to escape from the catalyst and appear in the product.

U.S. Pat. No. 4,417,086 describes a fluidized bed oligomerization process wherein periodically the flow of feed into the reaction zone may be stopped and the product may continue to be stripped from the catalyst with a stripping gas, which may be nitrogen. The oligomerization feed needs to contain gaseous olefins, and the oligomerization is operated with the olefin feedstock in the gas phase. The activity in such a gas phase oligomerization is significantly lower than with the oligomerization processes where the olefin feedstock is either partially or entirely in the liquid phase, or in the supercritical condition. The gas phase process therefore typically operates at a higher temperature as compared with these other processes, typically above 300° C., where side reactions become significant, such as cracking, olefin disproportionation, hydrogen transfer and dehydrocyclization. These side reactions cause the formation of byproducts such as paraffins, polyunsaturates, aromatics and olefins of other carbon numbers than the true oligomers of the feedstock olefins. These byproducts are acceptable, or even desirable, in certain product uses such as in transportation fuels, but they represent an undesired selectivity loss, and often an unacceptable product contamination, when the oligomer products are intended for the production of chemical derivatives such as alkylates or oxo-alcohols for plasticizers or detergents. In the gas phase oligomerization process of U.S. Pat. No. 4,417,086, the oligomers formed do not readily come off the catalyst, and they therefore are particularly prone to participate in these side reactions. Some of the byproducts, such as the aromatics, are intermediates for the formation of a particular kind of "coke", containing single and multiring aromatics. That aromatic-containing "coke" is hard to remove from molecular sieve catalysts, and when such deactivated catalysts are rejuvenated, temperatures of above 300° C. are required. There is even no evidence in U.S. Pat. No. 4,417,086 that the rejuvenation at 316° C. is effective in removing also the polynuclear aromatic coke present on the catalyst or trapped in the catalyst pores. Since the typical operating conditions of the gas phase oligomerization process are in the same range, also above 300° C., the equipment complies with the design requirement suitable for this temperature range and the necessary auxiliary equipment is in place and adequate to reach those temperatures. The rejuvenation with inert gas above 300° C. therefore does not create an additional burden or complexity on a gas phase oligomerization process.

Oligomerization processes using molecular sieve catalysts at conditions wherein the feedstock is partially or entirely in the liquid phase or in the supercritical or dense phase condition typically operate at temperatures of 300° C. and below. This suppresses side reactions such that higher selectivities to desired true oligomers can be achieved, and the products are of high purity, suitable for the production of chemical derivatives such as alkylates or oxo-alcohols for plasticizers or detergents. Equally important, the carbonaceous deposits formed under these conditions have been found to be predominantly non-aromatic, and to have a hydrogen to carbon atom ratio of between 1.6 and 2.0. If the higher temperature rejuvenation process known from the gas phase oligomerization process, i.e. above 300° C., are to be applied, additional requirements are put on the equipment designs and on the auxiliary equipment that are not needed for the oligomerization process itself.

The same applies even more to processes for the alkylation of an aromatic compound with an olefinic alkylating agent. The operating temperatures of these processes are typically similar to those of liquid or dense phase oligomerization when the olefinic alkylating agent is ethylene, and even lower when the olefinic alkylating agent is propylene or a normal butene such as butene-1 or butene-2. Alkylation of an aromatic compound with an olefinic alkylating agent is carried out in both liquid and vapour phase reactor systems. The rejuvenation method of the invention is believed to be more suitable for liquid phase operation because of the lower process temperatures.

There therefore remains a need for a rejuvenation method, applicable to molecular sieve catalysts aged, i.e. deactivated, by use in an olefin oligomerization process under conditions whereby the feedstock is in the liquid phase or in the supercritical condition, or aged, i.e. deactivated, by use in a process for the alkylation of an aromatic compound with an olefinic alkylating agent, that does not bring with it the additional requirements on the equipment designs nor the need for auxiliary equipment that is not needed for the oligomerization or alkylation process itself.

We have now found that the high molecular weight carbonaceous deposits in the oligomerization processes wherein the feedstock is in the liquid phase or in the super-critical condition, or in a process for the alkylation of an aromatic compound with an olefinic alkylating agent, is different and of a softer, non-aromatic nature, and that the molecular sieve catalysts deactivated by use in such processes can be rejuvenated at milder conditions at or below 300° C. This means that the need for more stringent equipment design criteria and for extra auxiliary equipment can be avoided.

There remains a need for a method that rejuvenates a molecular sieve catalyst that has been deactivated by, for example, a feedstock contaminated with sulphur and/or nitrogen compounds.

EP-A-716 887 describes reactivating a solid acid catalyst, in particular a solid phosphoric acid catalyst, in situ by subjecting it to sub-atmospheric pressure, removal of material released by this means optionally being assisted by introducing an inert gas, e.g., nitrogen, into the reactor while evacuating.

In a number of other prior proposals, e.g., EP-A-1 070 694 and U.S. Pat. No. 4,560,536, nitrogen is used to purge a catalyst bed before regeneration or rejuvenation, for example by burning with oxygen or solvent-extraction.

However, these references neither disclose nor suggest that the contact with nitrogen would itself, i.e., without the necessity of any other treatment, effect rejuvenation. Indeed, from the conditions of contact with nitrogen disclosed (for example, the low partial pressure inherent in the procedure mentioned in EP-A-716 887 and the scavenging conditions of the other two references) when compared with the intensity of the treatments that follow, it seems unlikely that any significant reaction was to take place between the nitrogen and the catalyst as such.

SUMMARY OF THE INVENTION

In a first aspect, the present invention provides a method of rejuvenating a molecular sieve catalyst, deactivated by use in an olefin oligomerization process under conditions whereby the feedstock is in the liquid phase or in the supercritical condition or by use in a process for the alkylation of an aromatic compound with an olefinic alkylating agent, which method comprises contacting the deactivated catalyst with an inert gas at an elevated temperature of at most 300° C. and at superatmospheric pressure for a time sufficient to effect an increase in catalytic activity of the deactivated catalyst. The catalytic activity that is increased is that for oligomerization or alkylation, as the case may be.

DETAILED DESCRIPTION OF THE INVENTION

The terms "supercritical" and "dense" as related to a fluid phase or conditions are terms that are herein used interchangeably. Both refer to a fluid at a temperature and a pressure above its thermodynamic critical point. The pressure-temperature phase diagram for a pure substance typically shows the conditions where liquid and vapor may coexist as a line ending in a maximum at what is defined as the thermodynamic critical point. The same diagram looks different for a mixture of compounds that have different boiling points. When for such a mixture, the initial boiling point temperatures and the initial dew point temperatures for the same pressures are traced, so as to envelop the two-phase region where vapor and liquid may coexist, typically a tear- or bell-shaped curve is obtained. The thermodynamic critical point is then defined as where the two-phase envelope reaches a maximum in pressure. The critical pressure is thus defined as the pressure above which no two-phases may coexist at any temperature. The critical temperature is then defined as the temperature at which the two-phase envelope reaches that maximum pressure.

It has unexpectedly been found that a molecular sieve oligomerization or alkylation catalyst deactivated by a sulphur compound-containing feedstock may be rejuvenated by treatment with an inert gas at an elevated temperature of at most 300° C. Accordingly, in a second aspect, the present invention provides the use of contact with an inert gas at an elevated temperature of at most 300° C. and preferably at superatmospheric pressure to rejuvenate a molecular sieve catalyst deactivated by a sulphur-compound and/or nitrogen-compound contaminated feedstock.

In both aspects, rejuvenation may be repeated after further catalyst use and resultant deactivation, and such repetition may be carried out one or more times.

As molecular sieves to be rejuvenated, there may be mentioned silicoaluminates, or true zeolites, for example, ZSM-5, ZSM-11, ZSM-12, ZSM-21, ZSM-22, ZSM-23, ZSM-35, ZSM-38, ZSM-45, ZSM-48, ZSM-57, MCM-22, MCM-49 and zeolites 13, A, X and Y. Apart from zeolites proper, there may be mentioned silicoaluminophosphates and aluminophosphates (SAPO's and ALPO's), especially SAPO-18, 34, 35, 44, 47 and ALPO-5, 11, 18, 31, 34, 36, 37, and 46 and the metal-containing forms thereof. The catalyst may be in any form, especially those typically used in hydrocarbon conversions, for example as a powder or extrudate.

The invention is especially advantageous for rejuvenating catalysts effective for olefin oligomerization under conditions whereby the feedstock is in the liquid phase or in the supercritical condition, more especially ZSM-22, ZSM-57, and MCM-22. It has unexpectedly been found that in such olefin oligomerization a rejuvenated catalyst has a higher selectivity than virgin catalyst to trimer, as opposed to dimer, formation, for example, a better selectivity to nonene in propene oligomerization.

The present invention accordingly also provides a process for the oligomerization of an olefinic feedstock under conditions whereby the feedstock is in the liquid phase or in the supercritical condition, which comprises contacting the feedstock under oligomerization conditions with a molecular sieve catalyst that has been rejuvenated by contact with an inert gas at an elevated temperature of at most 300° C. and at superatmospheric pressure.

The invention also provides the use in olefin oligomerization under conditions whereby the feedstock is in the liquid phase or in the supercritical condition of a molecular sieve catalyst that has been rejuvenated by contact with an inert gas at an elevated temperature of at most 300° C. to enhance selectivity to trimer, especially nonene, formation.

The invention is also applicable for rejuvenating catalysts effective for the alkylation of an aromatic compound with an olefinic alkylating agent, more especially MCM-22 and MCM-49. The catalyst in these processes is particularly sensitive to contact with water, especially during regeneration, as this has the effect that the selectivity to mono-alkylated products is reduced and more di- and sometimes also tri-alkylated products are formed. The rejuvenation method of the invention desirably does not contact water with these catalysts, so that the selectivity to the typically desired mono-alkylated product is better maintained.

The present invention accordingly also provides a process for the alkylation of an aromatic compound with an olefinic alkylating agent, which comprises contacting the feedstock under alkylation conditions with a molecular sieve catalyst that has been rejuvenated by contact with an inert gas at an elevated temperature of at most 300° C. and at superatmospheric pressure.

The olefinic alkylating agent may be for example ethylene, propylene, or one or more butenes, such as isobutylene, n-butene-1, or n-butene-2. It may also be a mixture of n-butenes, or it may even be a mixture of butenes with propylene. The aromatic compound may be for example benzene or naphthalene, or a substituted benzene or naphthalene. It may also be phenol.

The alkylation of the aromatic compound may be for example operated at a temperature of between 100° C. and 300° C., preferably between 110° C. and 250° C. With ethylene the temperature may be between 180° C. and 240° C. With propylene the alkylation temperature may be between 110° C. and 180° C., preferably at most 160° C.

These processes are typically operated with a fixed catalyst bed, and this may be arranged in a tubular or in a chamber reactor. The processes are typically operated in continuous mode.

As indicated above, the method is carried out at elevated temperature, and the temperature referred to is that in the vessel in which the reaction is being carried out. In this specification, except in the case where $CO_2$ is used as the inert gas, by elevated temperature is meant a temperature of at least 60° C. and advantageously a temperature in the range 60° C. to less than or equal to 300° C. (in contrast to regeneration, which is generally carried out at higher temperatures, e.g., 350° C. to 550 or even 750° C.). More especially the temperature is advantageously at least 100°, preferably at least 150° C., and more preferably at least 155° C. and even more preferably at least 200° C. Advantageously, and especially where the reaction being catalysed is oligomerization, the rejuvenation temperature is below 300° C., and preferably at most 250° C.

According to all aspects of the invention, excluding when supercritical $CO_2$ is used as the inert gas, the preferred temperature range within which the elevated temperature for rejuvenation is contained is from 100° C. to 300° C., more preferably from 150° C. or 155° C. to 250° C.

Rejuvenation is carried out at a pressure (in this specification the references are to absolute pressure unless otherwise stated) greater than atmospheric, i.e., at least or greater than 1 bar, 100 kPa. Advantageously, the pressure is at least 150 kPa, and preferably at least 500 kPa. Advantageously, the pressure is at most 8 MPa, preferably at most 5 MPa, more preferably at most 2 MPa, and most preferably at most 1 MPa, excluding when supercritical $CO_2$ is used as the inert gas.

In embodiments of the invention where the inert gas is a compound that may undergo phase transition under the temperature/pressure conditions mentioned above (see later discussion where the inert gas may be e.g. a hydrocarbon) the applied conditions are ideally in the supercritical region.

The preferred pressure, excluding when supercritical $CO_2$ is used, at which rejuvenation is carried out is within the range of from 150 kPa to 2 MPa absolute, more preferably from 500 kPa to 1 MPa.

Advantageously, and particularly when the inert gas is nitrogen, gas flow is at a VHSV of at least 2 $hr^{-1}$, and preferably at least 5 $hr^{-1}$. Advantageously gas flow is at a volume hourly space velocity (VHSV) of at most 10 $hr^{-1}$, and preferably at most 7 $hr^{-1}$.

The rejuvenation method should be carried out in the substantial absence of substances that deleteriously affect rejuvenation. Advantageously, the inert gas supply is substantially free from oxygen, in which context is required that the supply contains less than 0.5% by volume of oxygen. The inert gas is advantageously also substantially free from sulfur compounds, in which context is required that the supply contains less than 1 ppm by weight sulphur compounds measured as sulphur.

As inert gas, there is advantageously used nitrogen. However, since the gas employed functions as a carrier, any gas that does not react with the deactivated catalyst under the applied conditions ("inert gas") may be used. Such gases include those that are commonly termed "inert gases" in chemistry textbooks, and the noble gases as in group 18 of the Periodic Table of the Elements (see Chemical and Engineering News, 63(5), 27, 1985).

An inert gas that also may be used, is $CO_2$. In an alternative embodiment, the rejuvenation may be executed with $CO_2$ in a supercritical condition. The rejuvenation pressure in this embodiment should be at least 7.4 MPa, preferably at least 7.6 MPa, more preferably at least 7.8 MPa, yet more preferably at least 8 MPa and most preferably at least 8.5 MPa. It is preferable that the pressure is not more than 10 MPa. The rejuvenation temperature when $CO_2$ is used as the inert gas, which temperature is defined herein as "elevated", should be at least 32° C., preferably at least 35° C., more preferably at least 40° C., yet more preferably at least 60° C. and most preferably at least 100° C. It is preferable that the temperature is at most 250° C., preferably at most 200° C., more preferably at most 175° C. and even more preferably at most 150° C. in these embodiments that use $CO_2$ as the inert gas.

In a catalysed conversion process, as the activity of a catalyst is reduced, as a result of build-up of high molecular weight reaction products (coke), poisoning of active sites by feedstock contaminants, or usually both, it is common practice to maintain conversion rate, measured in a continuous process by the percentage of active feedstock reactants converted to product, as nearly constant as possible by increasing the reaction temperature. Advantageously the maximum permitted increase is by 50 degrees C., more advantageously by 25 degrees C., and preferably by 15 degrees C. The maximum temperature is limited by a number of factors, including most importantly usually catalyst selectivity, but also including reactor design, especially the practicality of using boiling water as the cooling medium, and the increase in coke formation at higher temperatures. Reactor temperatures are usually in the 100° C. to 350° C. range, with olefin oligomerization being usually in the 120° C. to 300° C. range, more especially 150° C. to below 300° C.

Concomitantly, the extent of rejuvenation, i.e. the increase in catalytic activity, is observable by a reduction in the temperature required for the catalysed reaction to proceed at a given conversion rate, with other conditions, e.g. reactant flow rate, being kept constant. Advantageously, the required reaction temperature after rejuvenation, for a given conversion rate and with other conditions being kept constant, is at least 5 degrees C., preferably at least 10 degrees C., and more preferably at least 25 degrees C. below that required before rejuvenation.

It has been found that rejuvenation is the more effective the less the extent to which deactivation has been allowed to proceed, and the invention accordingly also provides a method of carrying out a reaction catalysed by a molecular sieve catalyst which comprises interrupting the reaction after the temperature required to carry out the reaction under otherwise constant conditions has risen by at most 50 degrees C., advantageously at most 40 degrees C., and preferably at most 30 degrees C., and rejuvenating the deactivated catalyst by contact with an inert gas at elevated temperature and at superatmospheric pressure, to increase its catalytic activity, optionally repeating the cycle of reaction and rejuvenation one or more times.

In a variation of the method, presently not preferred, when the catalysed process is olefin oligomerization or alkylation, the inert gas is a substantially sulphur-free hydrocarbon, especially an alkane, advantageously at superatmospheric pressure. Optionally, the alkane is in admixture with the olefin or olefins being oligomerized or alkylated, in which case the rejuvenation temperature is advantageously below 100° C., so that the oligomerization and/or alkylation reaction does not take place during rejuvenation.

The rejuvenation method of the invention has the advantage that it may readily be carried out in situ if desired. When it is observed that catalytic activity has been reduced, as indicated by an unacceptable increase in required operating temperature to achieve a desired conversion rate, the reactant feedstock may be replaced by inert gas.

Treatment of deactivated catalyst by inert gas, even at the temperature of at most 300° C., may be for certain conditions of catalyst and olefin feed selection and the operating conditions of the oligomerization process very effective, and accordingly may be the sole treatment of the catalyst before being returned to service. However, it is also within the scope of the invention to use the method of the invention prior to catalyst regeneration by other methods, for example, those known in the art.

The following Example illustrates the invention, parts and percentages being by weight unless otherwise indicated.

Example

A liquid feedstock of 50 wt % propene/50 wt % butane was saturated with water by passing it through a vessel containing water at 39° C. The feed was preheated and then passed downward through a tubular reactor containing catalyst (11.6 g H-ZSM-57, particle size within the range 0.25 to 1.18 mm) at a pressure of 70 barg (69 bar, 6.9 MPa absolute) at a constant weight hourly space velocity of 2 hr$^{-1}$. At the reactor outlet, the effluent was cooled to room temperature, depressurized to 20 barg, and a sample injected into a gas chromatograph for determination of conversion rate and carbon number ($C_n$) distribution.

After running the reactor for several days with pure feed, during which the temperature was increased from its initial value of 150° C. to 168° C. to maintain the desired conversion rate, catalyst deactivation by a sulphur-containing feedstock was effected by using the following feed:

44.3 wt % propene-3.6 wt % butene-19.6 wt % propane-28.5 wt % butane with 10 ppm wt sulphur compounds. After two days on this sulphur-containing feed the catalyst activity had been substantially reduced, as shown by the Table below.

The original (pure) feedstock supply was resumed, and the reactor temperature increased to remove sulphur compounds and improve conversion rate. After 5 more days (on the resumed pure feed), when the temperature had reached 187° C., the feed supply was interrupted, the reactor temperature increased to 230° C., and nitrogen at 1.5 bar and a VHSV of 10 hr$^{-1}$ passed through the catalyst bed for 4 hours. The pure propene/butene feed and feed rate was then resumed and the reactor temperature could then be reduced to 149° C., while still maintaining the desired conversion rate of at least 90%. The Table below shows the results.

TABLE

| Days on Stream | Reactor Temp. ° C. | Conv. % | Selectivity to $C_9$, % | Feed |
|---|---|---|---|---|
| 0 | 150 | — | — | Original |
| 8.6 | 168 | 94.1 | 66.9 | Original |
| 12.6 | 168 | 95 | 71.2 | Original |
| 13.6 | 166 | 56.4 | 57.5 | Sulphur Contaminated |
| 14.6 | 166 | 5.5 | 13.6 | Sulphur Contaminated |
| 15.6 | 166 | 7 | — | Original |
| 16.6 | 166 | 17.2 | 38.5 | Original |
| 19.6 | 170 | 52.8 | 65.4 | Original |
| 20.6 | 180 | 79.6 | 65.4 | Original |
| 21.6 | 187 | 96.9 | 61.4 | Original |
| 22 | 230 | — | — | Nitrogen Treatment |
| 22.8 | 149 | 91.6 | 77.6 | Original |

The results show that the brief nitrogen treatment increases the conversion rate and the selectivity to trimer.

We claim:

1. A process for rejuvenating a molecular sieve catalyst, deactivated by use in a fixed bed olefin oligomerization process, the rejuvenation process comprises interrupting the oligomerization process after the temperature required to carry out the reaction under otherwise constant conditions has risen by at most 50 degrees C. and contacting the deactivated catalyst with a gas consisting essentially of nitrogen gas at an elevated temperature of at most 300° C. and at superatmospheric pressure for a time sufficient to effect an increase in olefin selectivity and catalytic activity of the deactivated catalyst; wherein the rejuvenated catalyst has a higher trimer selectivity than virgin catalyst.

2. The process according to claim 1 wherein the molecular sieve comprises a compound selected from the group consisting of ZSM-22, ZSM-57, MCM-22, MCM-49 and mixtures thereof.

3. The process according to claim 1 wherein rejuvenation is carried out at an elevated temperature in the range of from 100° C. to 300° C.

4. The process according to claim 3 wherein the temperature is in the range of from 150° C. to 250° C.

5. The process according to claim 1 wherein rejuvenation is carried out at a superatmospheric pressure in the range of from 150 kPa to 2 MPa.

6. The process according to claim 5 wherein the pressure is in the range of from 500 kPa to 1 MPa.

7. The process according to claim 1 wherein the rejuvenation pressure is at least 7.4 MPa and at most 10 MPa.

8. The process according to claim 1 wherein the molecular sieve catalyst is deactivated by a feedstock contaminated with a compound selected from a sulphur compound, a nitrogen compound, and mixtures thereof.

9. A method for enhancing selectivity to trimer formation in an olefin oligomerization process under conditions selected from conditions whereby the feedstock is in the liquid phase and conditions whereby the feedstock is in the supercritical condition, comprising contacting the olefin feedstock with a molecular sieve catalyst that has been rejuvenated by the process according to claim 1.

10. A process for the oligomerization of an olefinic feedstock, which comprises contacting the feedstock under oligomerization conditions selected from the group consisting of conditions whereby the feedstock is in the liquid phase and conditions whereby the feedstock is in the supercritical condition, with a fixed bed of a molecular sieve catalyst that has been rejuvenated by the process according to claim 1.

11. The process according to claim 10 which comprises repeating the cycle of reaction and rejuvenation at least one time.

12. The process according to claim 1 wherein the trimer selectivity of the deactivated catalyst after rejuvenation is at least 75.0%.

13. The process according to claim 1 wherein the trimer selectivity of the deactivated catalyst after rejuvenation is at least 77.0%.

14. The process according to claim 1 wherein the trimer selectivity of the deactivated catalyst after rejuvenation is at least 77.6%.

15. The process according to claim 1 wherein the gas is nitrogen gas.

* * * * *

UNITED STATES PATENT AND TRADEMARK OFFICE
CERTIFICATE OF CORRECTION

PATENT NO. : 8,691,713 B2
APPLICATION NO. : 11/912758
DATED : April 8, 2014
INVENTOR(S) : Dakka et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1597 days.

Signed and Sealed this
Eleventh Day of August, 2015

Michelle K. Lee
*Director of the United States Patent and Trademark Office*